(12) United States Patent
Sacedón Adelantado et al.

(10) Patent No.: US 6,873,672 B2
(45) Date of Patent: Mar. 29, 2005

(54) PROCEDURE AND DEVICE FOR MEASURING RESISTANCE TO HYDRIDING OF TUBES AND TUBULAR CLADDINGS

(75) Inventors: José Luis Sacedón Adelantado, Madrid (ES); Eduardo Santamera Gago, Madrid (ES); Marcos Díaz Muñoz, Madrid (ES); José Serafin Moya Corral, Madrid (ES); Elisa Román García, Madrid (ES); Angel Samuel Pérez Ramírez, Madrid (ES); Begoña Remartínez Zato, Madrid (ES)

(73) Assignees: Consejo Superior de Investigaciones Cientificas, Madrid (ES); Iberdrola, Madrid (ES)

( * ) Notice: Subject to any disclaimer, the term of this patent is extended or adjusted under 35 U.S.C. 154(b) by 0 days.

(21) Appl. No.: 10/388,328

(22) Filed: Mar. 13, 2003

(65) Prior Publication Data

US 2003/0185333 A1 Oct. 2, 2003

Related U.S. Application Data

(63) Continuation of application No. PCT/ES01/00350, filed on Sep. 14, 2001.

(30) Foreign Application Priority Data

Sep. 15, 2000 (ES) .......................................... 200002256

(51) Int. Cl.[7] .............................................. A21C 19/00
(52) U.S. Cl. ...................... 376/250; 376/256; 376/305; 376/306; 73/38; 208/107; 208/418
(58) Field of Search ................................ 376/245, 250, 376/256, 305, 306; 73/38, 40.7, 49.2; 208/107, 142, 418; 252/188.25, 188.26, 188.27; 423/644, 648, 248.1

(56) References Cited

U.S. PATENT DOCUMENTS

| | | | |
|---|---|---|---|
| 3,180,133 A | | 4/1965 | Rahme |
| 3,632,470 A | * | 1/1972 | Rubin et al. ................. 376/251 |
| 3,731,523 A | * | 5/1973 | Vissers et al. ............. 73/19.05 |
| 3,793,144 A | * | 2/1974 | Magladry .................... 376/421 |
| 3,943,751 A | * | 3/1976 | Akiyama et al. ........... 73/25.03 |
| 3,969,077 A | * | 7/1976 | Hill ............................... 436/3 |
| 3,977,232 A | * | 8/1976 | Hickam et al. ............. 73/19.05 |
| 3,994,778 A | * | 11/1976 | Grover et al. .............. 376/418 |
| 4,055,686 A | * | 10/1977 | Steinberg et al. ........... 427/124 |
| 4,119,488 A | * | 10/1978 | Barosi ........................ 376/418 |
| 4,451,445 A | * | 5/1984 | Cheng et al. ................ 423/645 |

(List continued on next page.)

OTHER PUBLICATIONS

Castelnau et al, 'Inservice monitoring and servicing after leak detection for the liquid–metal fast breeder steam generators of Phenix and Super–Phenix' Nuclear Technology, vol. 58, Aug. 1982, pp 171–183.*

Vissers et al 'A hydrogen monitor for detection of leaks in LMFBR steam generators' Nuclear Technology, vol. 12, Oct. 197 pp218–225.*

Primary Examiner—Michael J. Carone
Assistant Examiner—John Richardson
(74) Attorney, Agent, or Firm—Klauber & Jackson

(57) ABSTRACT

The method involves measuring hydrogen permeation in the tubes by mass spectrometry, wherein the tube is inserted into a high or ultrahigh vacuum device in which a mass spectrometer and a total pressure gauge are located. $H_2$ or $H_2$ and inert gas mixtures are circulated inside the tube at the required partial pressure. The tube is then heated and the appearance of $H_2$ outside the tube is observed. The flow thereof inside the tube and emergence time, called permeation time, are determined based on permeation curves. The emergence time of the first microcrack is also determined.

2 Claims, 3 Drawing Sheets

EXPERIMENTAL EQUIPMENT

U.S. PATENT DOCUMENTS

| | | | | |
|---|---|---|---|---|
| 4,652,420 A | * | 3/1987 | Smith | 376/256 |
| 4,761,553 A | * | 8/1988 | Juravic, Jr. | 250/298 |
| 4,916,076 A | * | 4/1990 | Johnson et al. | 436/6 |
| 5,114,664 A | * | 5/1992 | Terhune | 376/245 |
| 5,260,218 A | * | 11/1993 | Garde | 436/6 |
| 5,378,429 A | * | 1/1995 | Hayashi et al. | 422/53 |
| 6,067,844 A | | 5/2000 | Westbrook et al. | |
| 6,418,781 B1 | * | 7/2002 | Nishina et al. | 73/23.35 |
| 6,425,998 B1 | * | 7/2002 | Cholewa | 208/133 |
| 6,596,055 B2 | * | 7/2003 | Cooper et al. | 95/116 |

* cited by examiner though a secondary process. A case that has been known for some years is the hydriding of the tubular claddings of fuel in the cores of nuclear reactors, which is produced from the inner surface of the cladding as a consequence of a primary fault in their sealing weld. So far, the measurement of the resistance to hydriding of metals and alloys has been done by means of thermogravimetry and morphological studies of hydriding processes of metal pieces in an autoclave, which in some cases, such as the hydriding of tubular claddings of fuel, represents working conditions different from those in which the hydriding of the component takes place.

The determination of the resistance to hydriding of these tube components is of special economic relevance since the appropriate choice of the component would permit a reduction in the shutdowns of commercial reactors due to the secondary fault already mentioned. This possible improvement will also permit a greater utilisation of the fuel by making it more robust, and a diminution in the mass of high-activity nuclear waste for an equal amount of energy generated. By eliminating a source of fuel debris leak from the components of the reactor the radiation dose received by maintenance personnel and by whoever has to carry out operations in the energy interchange areas is thus reduced.

DESCRIPTION OF THE INVENTION

The present invention, as claimed, refers to a method of measuring the resistance to hydriding of tubes and tubular claddings and an apparatus arranged to measure said resistance to hydriding of tubes and tubular claddings.

The method of measuring the resistance to hydriding of tubes and tubular claddings is characterised by the following steps:

- inserting a tube to be tested in a chamber of a high or ultra-high vacuum equipment, said chamber containing a mass spectrometer and a total pressure gauge;
- passing hydrogen gas or a gas mixture of hydrogen and inert gas(es) into the interior of the tube, the permeation of hydrogen through the tube wall causing hydriding of the material thereof;
- heating said tube by Joule effect heating means;
- detecting hydrogen which has permeated through the wall of the tube at the exterior of the tube by means of the mass spectrometer or by measuring the total pressure in the chamber and determining a permeation time, on the basis of a permeation curve, i.e. a curve of quantity of hydrogen detected by the mass spectrometer against time, or total pressure detected against time, said permeation time being a time obtained from said permeation curve and representing the first appearance of hydrogen exterior of the tube, and;
- detecting a sudden rise in the total pressure, as an indication of the time of appearance of a first microcrack in the tube.

The apparatus arranged to measure the resistance to hydriding of tubes and tubular claddings is characterised by:

- a high or ultra-high vacuum equipment, having a chamber, said chamber containing a mass spectrometer and a total pressure gauge, and being provided with electrically insulating seals, which are flexible so as to absorb expansions;
- a gas line arranged to pass hydrogen gas or a gas mixture of hydrogen and inert gas(es) into the interior of the tube, the permeation of hydrogen through the tube wall causing hydriding of the material thereof;
- Joule effect heating means and thermocouples and temperature control means arranged to heat said tube in a controlled manner;
- the apparatus being arranged to detect hydrogen which has permeated through the wall of the tube at the exterior of the tube by means of the mass spectrometer or by measuring the total pressure in the chamber and determining a permeation time, on the basis of a permeation curve, i.e. a curve of quantity of hydrogen detected by the mass spectrometer against time, or total pressure detected against time, said permeation time being a time obtained from said permeation curve and representing the first appearance of hydrogen exterior of the tube, and;
- to detect a sudden rise in the total pressure, as an indication of the time of appearance of a first microcrack in the tube.

DESCRIPTION OF A PREFERRED EMBODIMENT OF THE INVENTION

The process and device for measuring the resistance to hydriding of tubes and tubular claddings of elements made of metal, metal alloys and any other material with and without protective coatings, comprises:

I) A procedure for determining the resistance to hydriding, at different temperatures, of tubes made of metal and other materials, with or without protective coatings.

Figure 1:
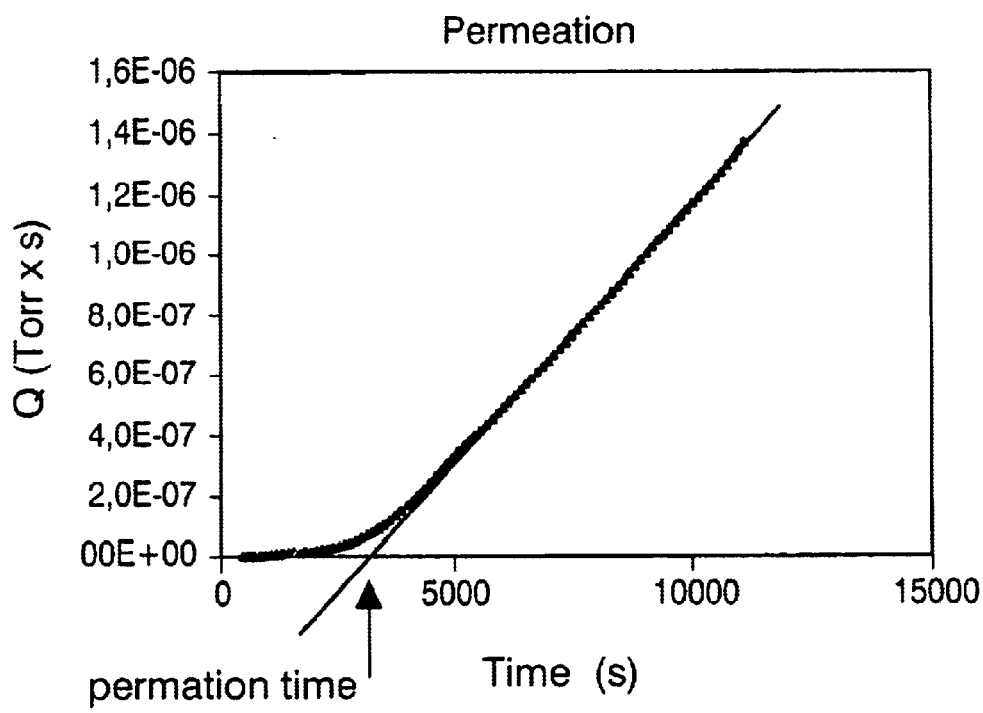
FIG. 1. Permeation curve and determination of the permeation time.
Figure 2:
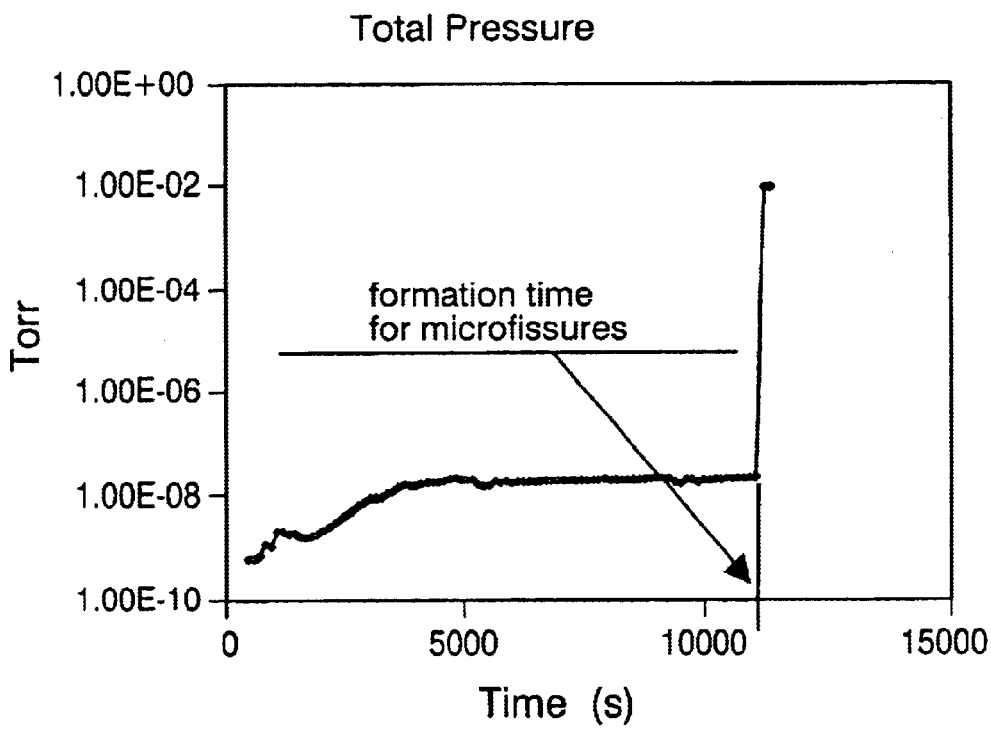
FIG. 2. Determination of the deformation time of the microcrack.
Figure 3:
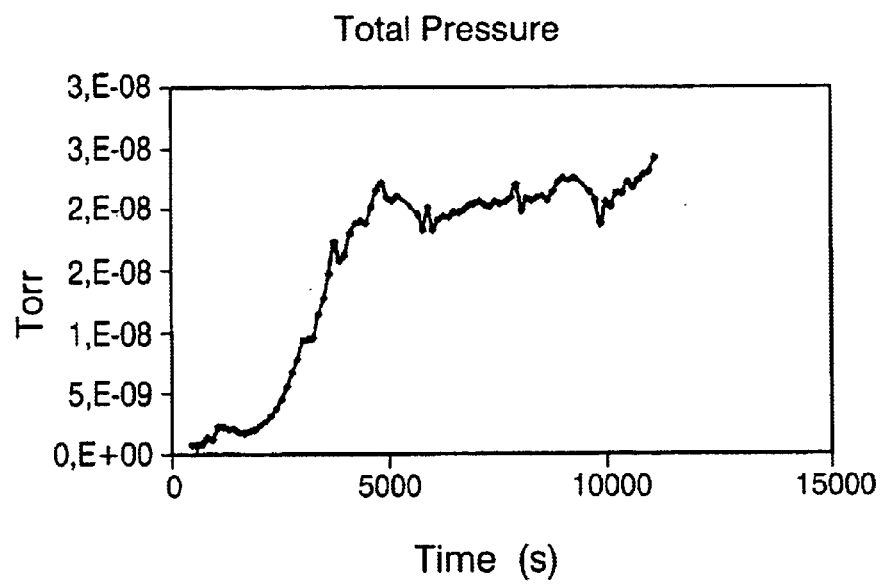
FIG. 3. Flow curve for total pressure.
Figure 4:
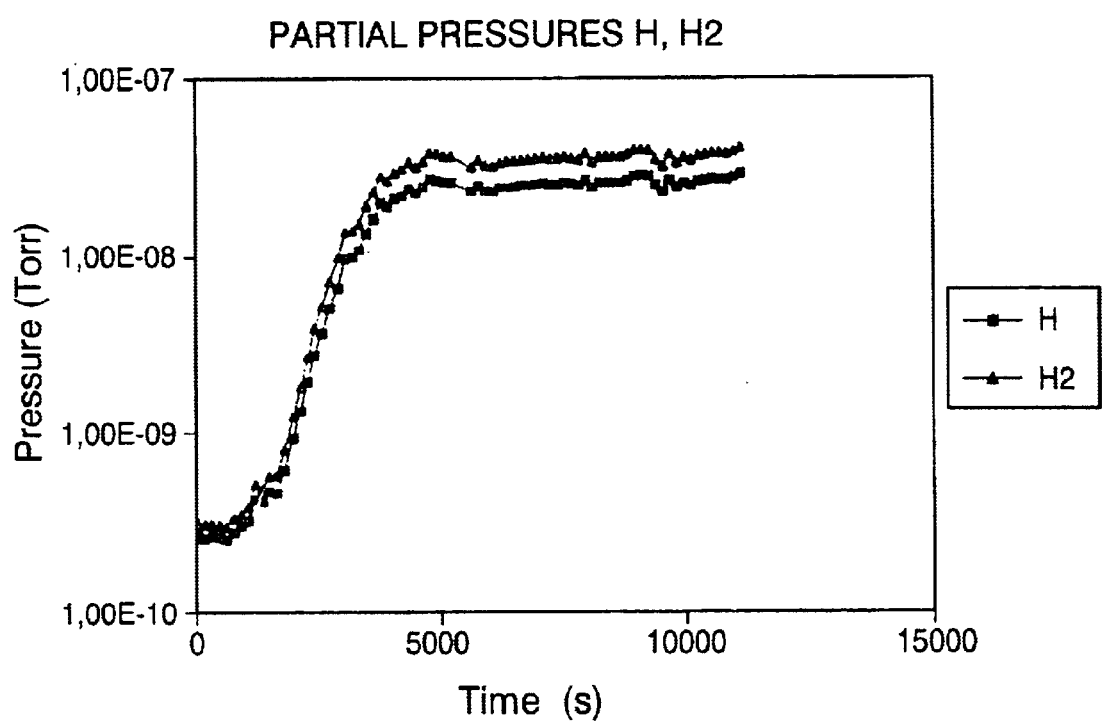
FIG. 4. Flow curve for partial pressures.

The procedure comprises measuring permeation of hydrogen in tubes by means of mass spectrometry, for which the tubes is inserted in high or ultra-high vacuum equipment containing a mass spectrometer and a total pressure gauge; hydrogen gas or mixtures of hydrogen gas and inert gas(es) is made to circulate through the interior at the required partial pressure. The tube heats up due to the Joule effect and the appearance of hydrogen gas in the exterior of the tube is observed by means of the mass spectrometer or the total pressure gauge, with its flow via the tube and its appearance time, called the permeation time, being determined on the basis of the permeation curves, FIG. 1. The determination is also made of the appearance time of the first microcrack, detected by the sudden rise of the total pressures, FIG. 2, or partial pressure of hydrogen gas in the high or ultra-high vacuum equipment. This also permits samples to be obtained just at the onset of the fracture process, which is very suitable for studying its formation. Furthermore, the system permits the application of longitudinal tensions and compressions. The measurement of the permeation time and appearance time for the first microcrack gives two measurements of the resistance of the tube to hydriding. The total pressure curves, FIG. 3, or partial pressure curves, FIG. 4, corresponding to the flow of hydrogen gas, as well as the permeation curves, FIG. 1, also permit a comparison of the hydriding process among different tubes.

II) The equipment constructed for carrying out that procedure.

Figure 5:
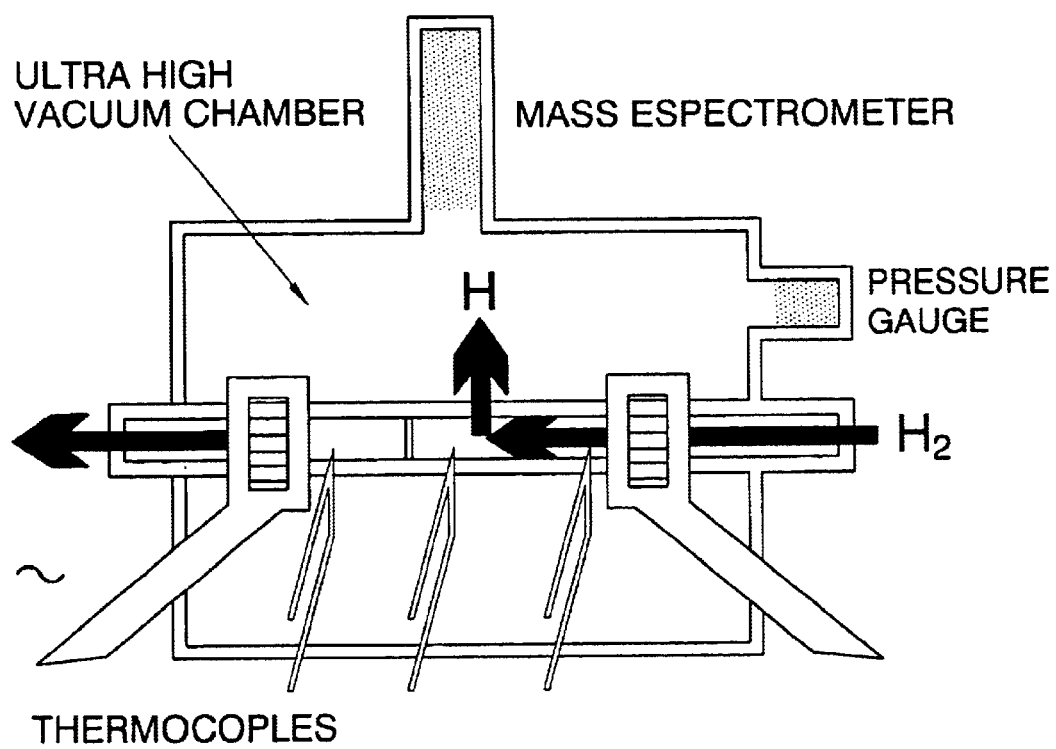
FIG. 5. Diagram of the device for measuring the resistance of tubes to hydriding.

The equipment (FIG. 5) comprises an ultra-high vacuum chamber with special seals adapted to the exterior diameter of the tube, these seals being flexible so that they can absorb expansions and being electrically insulated. Inside the chamber are the mass spectrometer and the total pressure gauge. The heating of the sample is done by the Joule effect and the temperature control is by means of thermocouples and control modules. The gas line for the circulation of hydrogen gas permits the purity of the gas to be kept at equal to or greater than 99.9999 mole percent. The mass spectrometer, as well as the gas line, is controlled by a computer. Both the equipment and the control and measurement programmes have been designed and constructed for this procedure, since there is no commercial equipment available having this objective, nor any other that could be adaptable.

The heating method followed here is the direct one, with the current being made to pass through the tube. This method reduces the degasification effect of other components to the minimum, and any indirect method can be used as an alternative. In our case, the tube is heated by an alternating current in order to prevent electromigration effects. Direct current can also be used in those cases in which this phenomenon is not expected. In the present device, one of the ends of the sample is secured by means of a flexible termination of the ultra-high vacuum chamber of the system, which, by means of a mechanical device, permits compensation of the longitudinal compression caused by atmospheric pressure. This mechanism also enables longitudinal tensions and compressions to be applied to the tube.

What is claimed is:

1. Method of measuring the resistance to hydriding of tubes and tubular claddings, meaning hydriding the formation of hydrides, characterized by the following steps:

inserting a tube to be tested through a chamber of ultra-high vacuum equipment, said chamber containing a mass spectrometer and a total pressure gauge;

passing hydrogen gas or a gas mixture of hydrogen and inert gas(es) into the interior of the tube, the permeation of hydrogen through the tube wall causing hydriding of the material thereof;

heating said tube by Joule effect heating means;

detecting hydrogen which has permeated through the wall of the tube at the exterior of the tube by measuring $H_2$ and H partial pressures in the chamber or by measuring the total pressure in the chamber and determining a permeation time on the basis of a permeation curve, i.e. a curve of quantity of hydrogen detected by measuring $H_2$ and H partial pressures in the chamber against time, or total pressure detected against time, said permeation time being a time obtained from said permeation curve and representing the first appearance of hydrogen exterior of the tube, and;

detecting a sudden rise in the total pressure, as an indication of the time of appearance of a first micro crack in the tube.

2. A method according to claim 1, characterized in that the tubes and tubular claddings are nuclear fuel tubes and tubular claddings used in cores of nuclear reactors.

* * * * *